(12) United States Patent
Park et al.

(10) Patent No.: US 12,186,565 B1
(45) Date of Patent: Jan. 7, 2025

(54) ULTRASONIC TRIBOELECTRIC GENERATING DEVICE AND ELECTROCEUTICAL FOR NERVE STIMULATION PROVIDED WITH SAME

(71) Applicant: ENERGY MINING Co., Ltd., Suwon-si (KR)

(72) Inventors: Hyun Moon Park, Suwon-si (KR); Young Wook Chung, Suwon-si (KR); Jang Mook Jeong, Suwon-si (KR); Joon Ha Hwang, Suwon-si (KR)

(73) Assignee: ENERGY MINING Co., Ltd., Suwon-si (KR)

( * ) Notice: Subject to any disclaimer, the term of this patent is extended or adjusted under 35 U.S.C. 154(b) by 0 days.

(21) Appl. No.: 18/587,579

(22) Filed: Feb. 26, 2024

(30) Foreign Application Priority Data

Dec. 27, 2022 (KR) .................. 10-2022-0186172
Feb. 21, 2023 (KR) .................. 10-2023-0022571
Feb. 21, 2023 (KR) .................. 10-2023-0022572

(51) Int. Cl.
*A61N 1/36* (2006.01)
*A61N 1/05* (2006.01)
*A61N 1/378* (2006.01)
*H02N 1/04* (2006.01)

(52) U.S. Cl.
CPC ....... *A61N 1/36125* (2013.01); *A61N 1/0556* (2013.01); *A61N 1/36071* (2013.01); *A61N 1/378* (2013.01); *H02N 1/04* (2013.01)

(58) Field of Classification Search
CPC .................. A61N 1/0556; A61N 1/3787
See application file for complete search history.

(56) References Cited

U.S. PATENT DOCUMENTS

| | | | |
|---|---|---|---|
| 2021/0308462 A1* | 10/2021 | Carmena | A61N 1/36139 |
| 2022/0161037 A1* | 5/2022 | Mueller | A61N 1/375 |
| 2023/0093932 A1* | 3/2023 | Kim | A61N 1/3787 310/310 |
| 2023/0135593 A1* | 5/2023 | Kim | A61N 1/378 310/300 |

FOREIGN PATENT DOCUMENTS

| | | |
|---|---|---|
| KR | 10-2011-0062219 A | 6/2011 |
| KR | 10-2017-0017565 A | 2/2017 |
| KR | 10-2021-0112552 A | 9/2021 |

OTHER PUBLICATIONS

"Written Decision On Registration" issued in KR 10-2023-0022571; mailed by the Korean Intellectual Property Office on Jun. 26, 2023.

(Continued)

*Primary Examiner* — George R Evanisko
(74) *Attorney, Agent, or Firm* — Studebaker & Brackett PC

(57) ABSTRACT

Disclosed is an ultrasonic triboelectric generating device and an electroceutical for nerve stimulation. A metal package is provided externally, an interface design between the metal package and the ultrasonic triboelectric generating device is improved to maximize power generation efficiency by ultrasonic waves, and a high power output may be continuously provided without a battery replacement process in various frequency bands.

7 Claims, 16 Drawing Sheets

(56) References Cited

OTHER PUBLICATIONS

"Request for the Submission of an Opinion" issued in 10-2023-0022572; mailed by the Korean Intellectual Property Office on Apr. 19, 2023.
"Written Decision on Registration" issued in KR 10-2023-0022572; mailed by the Korean Intellectual Property Office on Jun. 26, 2023.
Chen, et al.; Micro triboelectric ultrasonic device for acoustic energy transfer and signal communication; Nature Communications; vol. 11; No. 4143; Aug. 18, 2020; pp. 1-9.
Lee, et al.; Development of battery-free neural interface and modulated control of tibialis anterior muscle via common peroneal nerve based on triboelectric nanogenerators; Nano Energy; vol. 33; Jan. 10, 2017; pp. 1-11.

* cited by examiner

· TENG output by 20 kHz ultrasonic wave

ULTRASONIC TRIBOELECTRIC GENERATING DEVICE AND ELECTROCEUTICAL FOR NERVE STIMULATION PROVIDED WITH SAME

CROSS-REFERENCE TO RELATED APPLICATIONS

A claim for priority under 35 U.S.C. § 119 is made to Korean Patent Application Nos. 10-2022-0186172 filed on Dec. 27, 2022, 10-2023-0022571 filed on Feb. 21, 2023, and 10-2023-0022572 filed on Feb. 21, 2023, in the Korean Intellectual Property Office, the entire contents of which are hereby incorporated by reference.

BACKGROUND

1. Technical Field

The present disclosure relates to an ultrasonic triboelectric generating device and an electroceutical for nerve stimulation provided with the same, and more particularly, relates to an ultrasonic triboelectric generating device and an electroceutical for nerve stimulation provided with the same applied with a metal package and using a resonance-based grid structure.

2. Description of Related Art

Entering an aging society, the demand for implantable medical devices that are implanted into a human body to replace or assist some of the physical functions or to treat diseases is explosively increasing.

For example, the implantable medical devices into a human body include an artificial pacemaker, a deep brain stimulator (DBS), and a spinal cord stimulator (SCS).

These implantable medical devices operate based on a battery, and the surgery for battery replacement is required every certain cycle. Since such periodic surgery brings enormous mental and physical burdens to patients, the research on the development of wireless charging technology for the implantable medical devices is being actively conducted in the industry/academic community to solve the problem.

However, most medical devices inserted into a human body are biocompatible and are applied with an external package with a metal such as titanium that can secure stability, but the conventional wireless charging technology (NFC, RFID, etc.) using electromagnetic wave has a limitation in that it cannot transmit such metal packages. In addition, the conventional technology has a problem of unable to charge a device inserted deep into a body due to the limitation of the charging distance.

Ultrasonic wave is also widely used in a human body for imaging and treatment purposes and can transmit energy through a metal package such as titanium. However, a titanium package and device design that considers ultrasonic transmission efficiency and device power generation efficiency need to be preceded to pass through materials with high acoustic impedance such as titanium, and the Research related to this has been conducted very little so far.

In addition, the conventional wireless charging technology (e.g., NFC, RFID, etc.) using electromagnetic waves cannot charge devices inserted deep into a body due to the limitation of charging distance, and questions about human body stability are raised, making it difficult to use.

Therefore, a technology that charges implantable medical devices in a body using triboelectricity generated by ultrasonic waves, which is widely used in a human body for imaging and treatment purposes, is drawing attention as an alternative.

However, the ultrasonic frequency available in a body is limited in consideration of human body stability, and the ultrasonic energy transmitted to the device is more limited in consideration of ultrasonic attenuation by biological tissues and package materials. In addition, there is a problem in that the frequency band applicable to the ultrasonic triboelectric power generation device is limited because the displacement of the film generated as the ultrasonic frequency increases decreases, and the generated voltage also decreases according to the power generation principle of the triboelectric power generation device.

Therefore, it is necessary to design a device to stably generate sufficient power in various ultrasonic frequency bands.

This work was supported by the Next Generation Intelligence Semiconductor Foundation Program (20025736, Development of MICS SoC and platform for invivo implantable electroceutical device) funded By the Ministry of Trade, Industry & Energy (MOTIE, Korea)

This research was supported by the Bio & Medical Technology Development Program of the National Research Foundation (NRF) & funded by the Korean government (MSIT) (No. 2022M3E5E9016662).

This work (Grants No. S3282292) was supported by Business for Startup growth and technological development (TIPS Program) funded Korea Ministry of SMEs and Start-ups in 2022.

SUMMARY

An embodiment of the present disclosure is to provide an ultrasonic triboelectric generating device and an electroceutical for nerve stimulation provided with the same, which is provided with an external metal package, can improve an interface design between the metal package and the ultrasonic triboelectric generating device, and maximize the power generation efficiency by ultrasonic waves.

An embodiment of the present disclosure is to provide an ultrasonic triboelectric generating device which can supply high power output persistently without exchanging a battery in various frequency bands.

Technical problems of the inventive concept are not limited to the technical problems mentioned above, and other technical problems not mentioned will be clearly understood by those skilled in the art from the following description.

In an aspect, an ultrasonic triboelectric generating device applied with a metal package according to the present disclosure includes a lower electrode; a first friction member disposed on the lower electrode; a matching layer disposed on the first friction member; and a titanium package disposed to surround an outer periphery of a generating device module having the lower electrode and the first friction member as a group and attached to an upper portion of the matching layer to be included in the matching layer, the matching layer includes a fluid, performs a function of an upper electrode, and of which displacement occurs only on a surface facing the lower electrode by ultrasonic wave generated externally.

In this case, the titanium package may include an upper housing disposed to surround an upper portion and a side portion of the generating device module and attached to a side of the matching layer, and a lower housing partially inserted to the upper housing to surround a lower portion and the side portion of the generating device module.

Furthermore, the upper housing may include a storage block downwardly protruded to surround the matching layer in an inner surface thereof facing the matching layer.

Furthermore, the upper housing may further include a sealing member extended to cover from a front end of the storage block to a substrate, and attaching the lower housing and a silicon head disposed on at least a side of an outer surface of the titanium package.

Furthermore, the electricity generated by the power generating device module may be connected through a feedthrough when the electricity is transmitted to the silicon head and outside of the lower housing.

Furthermore, the first friction member may generate electricity by friction with the lower electrode when a displacement is caused by ultrasonic wave provided from outside.

Furthermore, the matching layer may be closely disposed to the first friction member, and of which shape may be deformed corresponding to a vibration of the first friction member.

Furthermore, the ultrasonic triboelectric generating device applied with a metal package according to the present disclosure may further include a spacer provided between the upper housing and the lower electrode, and the spacer may include a lower supporting member for supporting a portion between the first friction member and the lower electrode, an upper supporting member for supporting a portion between the first friction member and the upper housing, and a connection member disposed at least partially penetrating the first friction member to connect between the lower supporting member and the upper supporting member.

Furthermore, in another aspect, an electroceutical provided with an ultrasonic friction generating device according to the present disclosure includes the ultrasonic triboelectric generating device applied with a metal package; and a cuff electrode provided on a side of the titanium package and mounted on a nerve fiber, based on a nerve stimulation signal being generated in the nerve fiber, the triboelectricity generated by providing ultrasonic wave to the ultrasonic triboelectric generating device may be transferred to the nerve fiber through the cuff electrode, thereby blocking a transmission of the nerve stimulation signal to a brain.

Furthermore, in still another aspect, an ultrasonic triboelectric generating device using a resonance-based grid structure according to the present disclosure includes a substrate provided with a lower electrode; a grid member disposed on the lower electrode; and a first friction member disposed on the grid member, the first friction member is disposed corresponding to a configured pattern on the grid member and induces an electric charge by friction with the lower electrode when a displacement occurs by ultrasonic wave provided externally, the grid member includes a plurality of vibration areas having a same size corresponding to a first displacement area in which a displacement occurs in the first friction member and a plurality of fixed areas respectively disposed between the vibration areas, the grid member forms a cross section of the vibration area in a square shape, a side of the vibration area is set within 1 mm, a vibration displacement of the first friction member is up to 250 μm when the ultrasonic wave provided externally is 20 kHz bandwidth, and the vibration displacement is greater in a center than in a periphery thereof.

Furthermore, the ultrasonic triboelectric generating device using a resonance-based grid structure according to the present disclosure may further include a second friction member separately disposed from the first friction member on a lower portion of the grid member.

In this case, a displacement may occur in the first displacement area corresponding to the vibration area when the ultrasonic wave is provided externally, and the first friction member may rub against the second friction member.

Furthermore, the first friction member and the second friction member may have materials with contrasting charging properties.

Furthermore, the ultrasonic triboelectric generating device using a resonance-based grid structure according to the present disclosure may further include a protrusion provided in the fixed area to separate the first friction member or the second friction member from the grid member.

Furthermore, the first friction member or the second friction member may be integrally disposed to be supported at a front end of the protrusion, respectively, or the first friction member or the second friction member may be divided into multiple parts to correspond to the respective vibration area and mounted between the protrusions.

Furthermore, in still another aspect, an electroceutical provided with an ultrasonic triboelectric generating device according to the present disclosure includes the ultrasonic triboelectric generating device; and a cuff electrode provided on a side of the generating device and mounted on a nerve fiber, based on a nerve stimulation signal being generated in the nerve fiber, the triboelectricity generated by providing ultrasonic wave to the ultrasonic triboelectric generating device is transferred to the nerve fiber through the cuff electrode, thereby blocking a transmission of the nerve stimulation signal to a brain.

BRIEF DESCRIPTION OF THE FIGURES

The abstract described above as well as the detailed description of the preferred embodiment of the present disclosure described below will be better understood when read in connection with the accompanying drawings. For the purpose of illustrating the present disclosure, preferred embodiments are shown in the drawings. However, it should be understood that the present disclosure is not limited to the precise arrangement and means illustrated.

DETAILED DESCRIPTION

Figure 1:
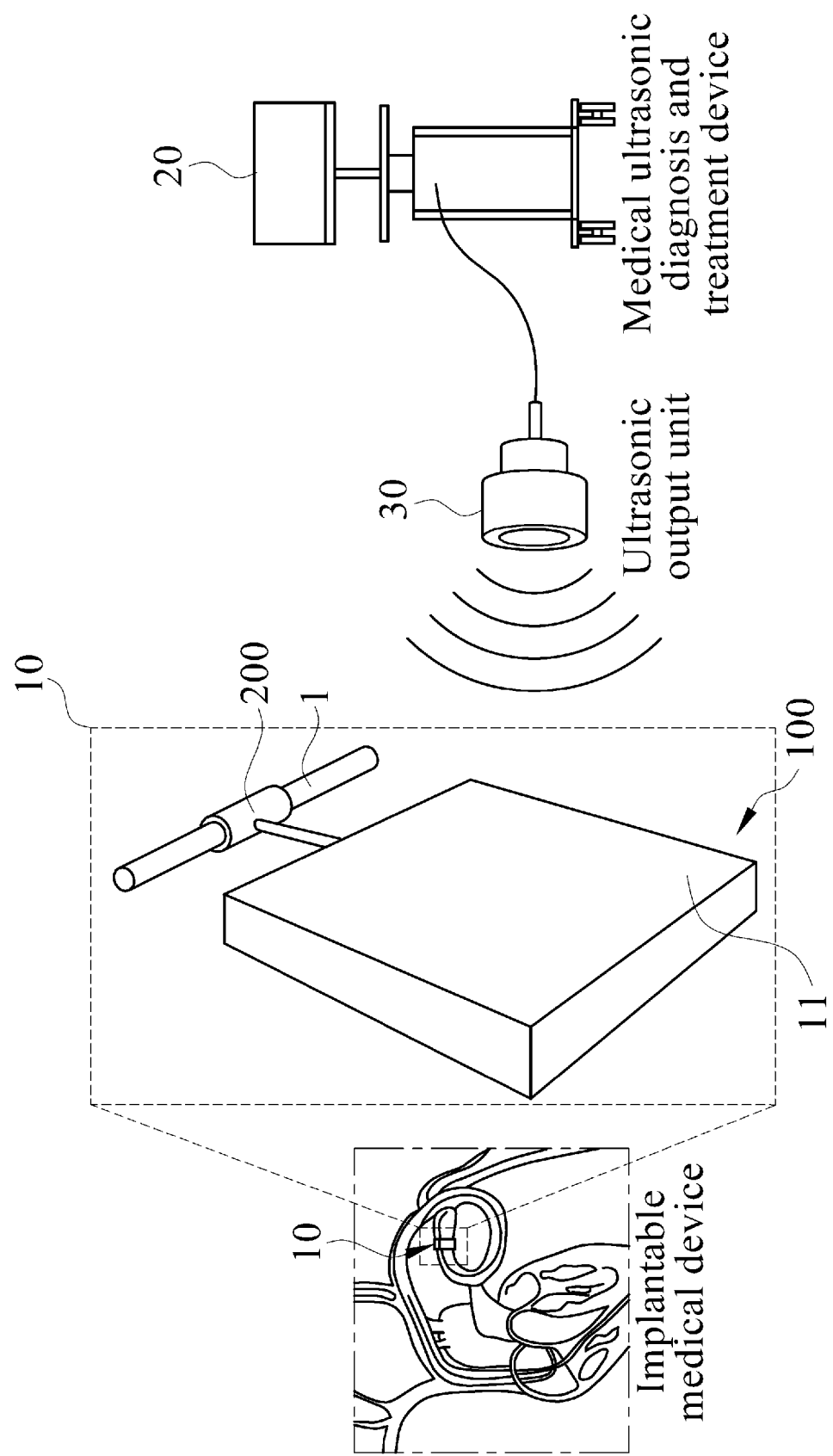
FIG. 1 is a diagram illustrating an overall system according to the present disclosure.

In the drawings, the same reference numeral refers to the same element. This disclosure does not describe all elements of embodiments, and general contents in the technical field to which the present disclosure belongs or repeated contents of the embodiments will be omitted. The terms, such as "unit, module, member, and block" may be embodied as hardware or software, and a plurality of "units, modules, members, and blocks" may be implemented as one element, or a unit, a module, a member, or a block may include a plurality of elements.

Throughout this specification, when a part is referred to as being "connected" to another part, this includes "direct connection" and "indirect connection", and the indirect connection may include connection via a wireless communication network. Furthermore, when a certain part "includes" a certain element, other elements are not excluded unless explicitly described otherwise, and other elements may in fact be included.

Furthermore, when a certain part "includes" a certain element, other elements are not excluded unless explicitly described otherwise, and other elements may in fact be included.

In the entire specification of the present disclosure, when any member is located "on" another member, this includes a case in which still another member is present between both members as well as a case in which one member is in contact with another member.

The terms "first," "second," and the like are just to distinguish an element from any other element, and elements are not limited by the terms.

The singular form of the elements may be understood into the plural form unless otherwise specifically stated in the context.

Identification codes in each operation are used not for describing the order of the operations but for convenience of description, and the operations may be implemented differently from the order described unless there is a specific order explicitly described in the context.

Hereinafter, operation principles and embodiments of the present disclosure will be described with reference to the accompanying drawings.

FIG. 1 is a diagram illustrating an overall system according to the present disclosure.

Referring to FIG. 1, an electroceutical for nerve stimulation 10 according to an embodiment of the present disclosure is a type of implantable medical devices, and may be implanted into a user's body or injected through an injection.

Of course, the electroceutical for nerve stimulation 10 are miniaturized and lightweight enough to be inserted into the body, and since there is no need for surgery for battery replacement, the mental and physical burden of surgery may be minimized, and drug treatment may be replaced while operating stably in the deep part of the body, and accordingly, there are advantages that may be applied to the treatment of various diseases.

To implement this, the electroceutical for nerve stimulation 10 according to the present disclosure may be provided with a titanium package 11 to secure stability in the body, and although it is not shown in the drawing, a separate coating layer (not shown) may be further provided externally. The coating layer may use silicon, for example.

The detailed description of the titanium package 11 will be described below.

The electroceutical for nerve stimulation 10 includes an ultrasonic triboelectric generating device (hereinafter, power generating device) 100 stored in the titanium package 11 and a cuff electrode 200.

Here, the detailed description related to the power generating device 100 will be described below.

The cuff electrode 200 may be extended from the power generating device 100 and selectively mounted on a nerve fiber 1. In this case, the cuff electrode 200 may be mounted in consideration of charge injection limit and charge injection efficiency to minimize the damage of nerve tissues. Furthermore, the cuff electrode 200 may be selectively mounted on a peripheral nerve, a nerve epithelium, a blood vessel, and the like.

In the case that the cuff electrode 200 is mounted in the body, ultrasonic waves are provided to the power generating device 100 from an ultrasonic output unit 30 connected to a medical ultrasonic diagnosis and treatment device 20 to induce energy generation characteristics using resonance from the power generating device 100, so that the electroceutical for nerve stimulation 10 generates a constant and strong displacement (electric signal or vibration), and direct disease treatment may be performed therethrough or the power of the implantable medical device for disease treatment may be charged.

Figure 2:
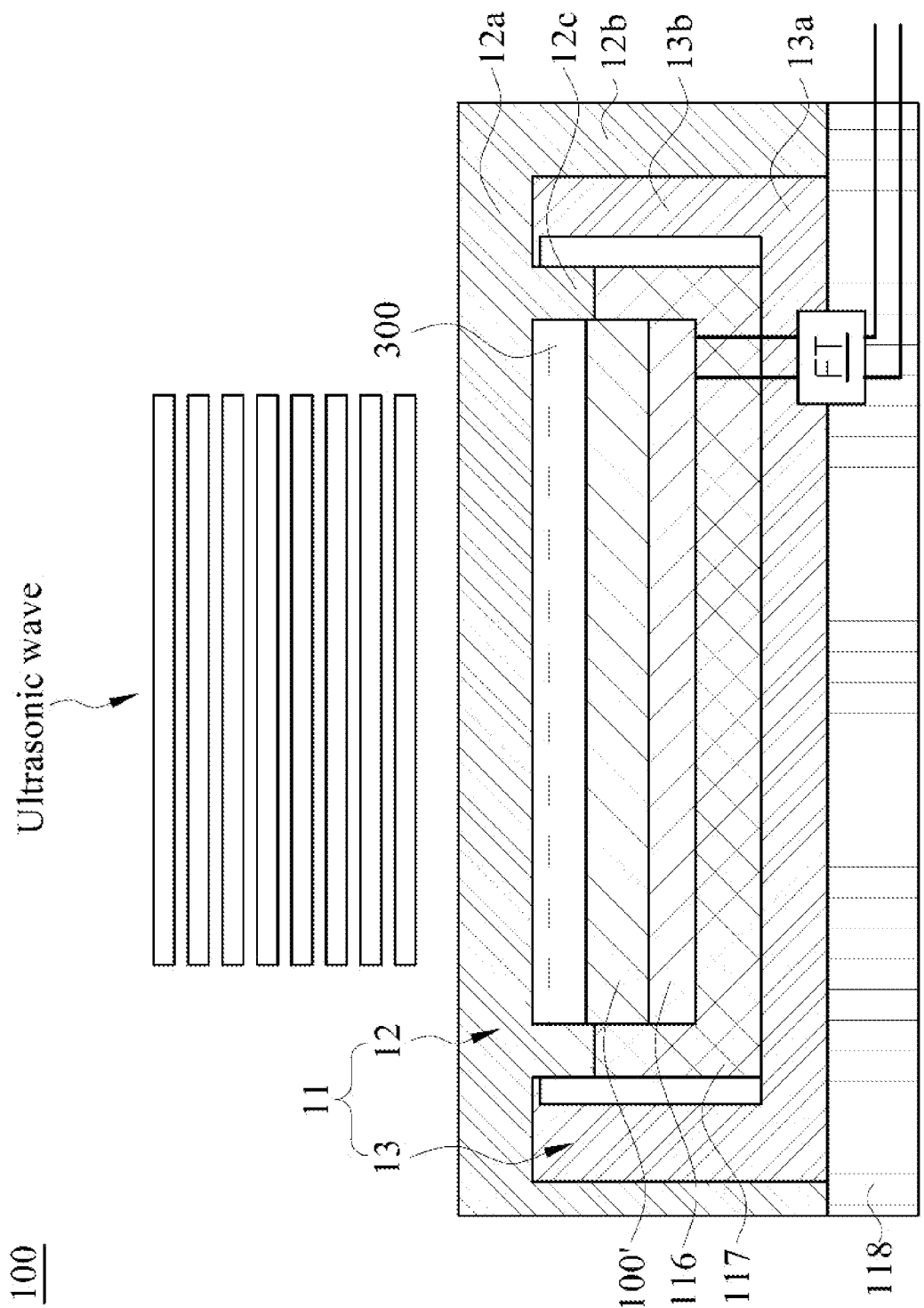
FIG. 2 is a sectional diagram illustrating an ultrasonic triboelectric generating device applied with a metal package according to the present disclosure.
Figures 3A, 3B:
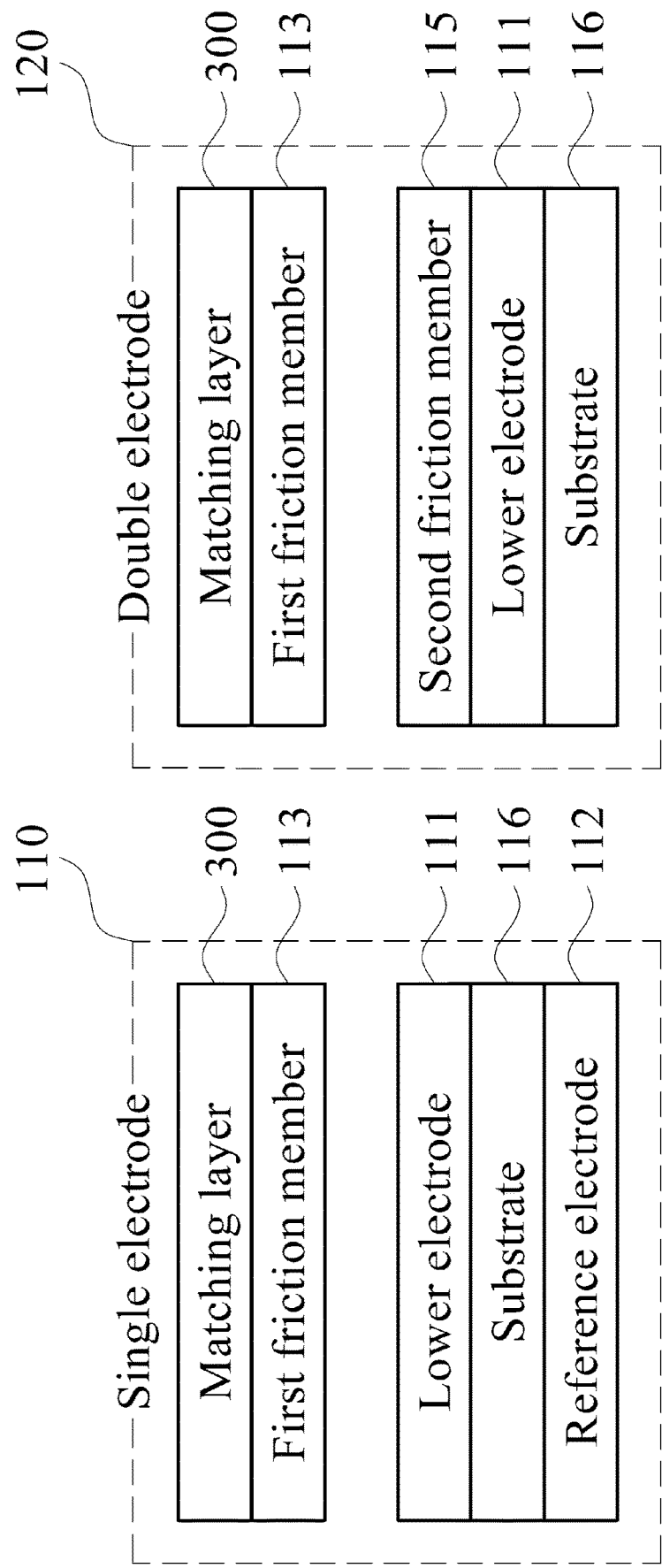
FIGS. 3A and 3B are block diagrams illustrating a module of an ultrasonic triboelectric generating device applied with a metal package according to the present disclosure.
Figure 4:
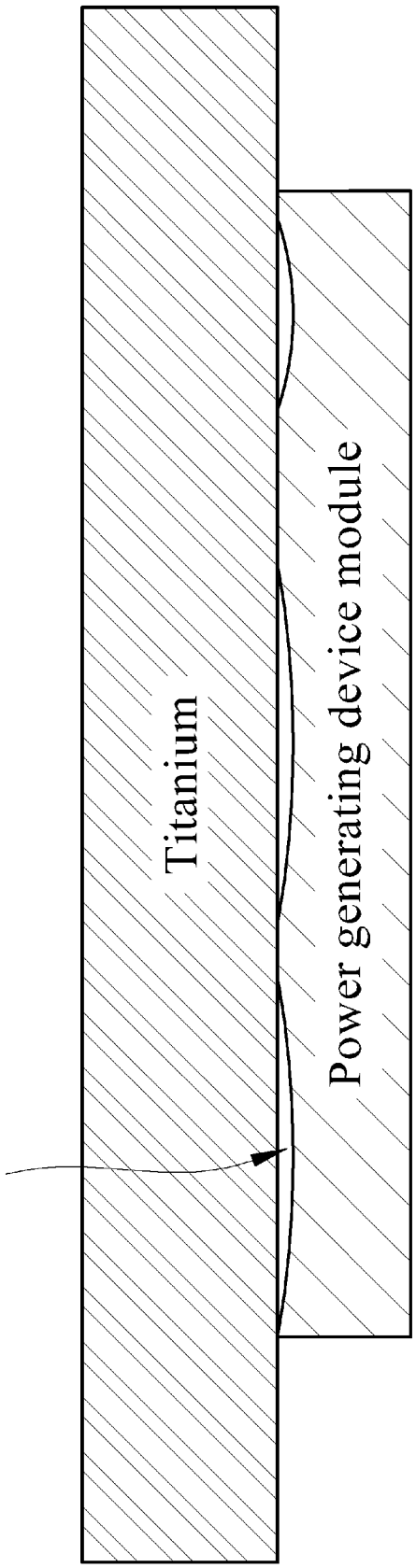
FIG. 4 is a reference diagram illustrating an interface between a general power generating device and a metal package.

FIG. 2 is a sectional diagram illustrating an ultrasonic triboelectric generating device applied with a metal package according to the present disclosure. FIGS. 3A and 3B are block diagrams illustrating a module of an ultrasonic triboelectric generating device applied with a metal package according to the present disclosure. FIG. 4 is a reference diagram illustrating an interface between a general power generating device and a metal package.

Referring to FIG. 2 to FIG. 4, the power generating device 100 according to the present disclosure includes a matching layer 300 provided in the titanium package 11 and a power generating device module 100'.

The titanium package 11 includes an upper housing 12 and a lower housing 13. For example, the titanium package 11 is manufactured by a titanium material for stability in the body, and the power generating device module 100' having an approximate hexahedral shape is embedded therein. Of course, the material of the titanium package 11 or the shape of the power generating device module 100' is not limited thereto, and simple design change is available with the same purpose and effect.

The upper housing 12 is attached to a side (e.g., top surface) of the matching layer 300 to contact closely. The upper housing 12 includes a top surface portion 12a corresponding to a side of the matching layer 300, a side surface portion 12b bent at a top end of the top surface portion 12a and extended to correspond a side area of the power generating device module 100', and a storage block 12c protruded from an inner bottom surface of the top surface portion 12a and forming a storage space to surround a periphery of the matching layer 300.

The upper housing 12 may have a vessel shape of which bottom side is open.

The storage block 12c provides a function of providing a regular (or a predetermined size of) storage space in preparation that the matching layer 300 is formed of a predetermined fluid excluding gas. In this case, the fluid may include any one of solid, semi-solid and liquid. Of course, the storage block 12c may be deformed depending on a shape of the power generating device module 100'. In addition, the storage block 12c may be formed to correspond to at least a height (or thickness) of the matching layer 300 or to have a higher height.

The lower housing 13 includes a bottom surface portion 13a covering a bottom side of the upper housing 12 corresponding to the top surface portion 12a and a side surface portion 13b bent at an end portion of the bottom surface portion 13a and inserted into the side surface portion 12b of the upper housing 12.

The lower housing 13 may have a vessel shape having a relatively small size compared to the upper housing 12 with an open top portion.

Accordingly, when the coupling of the upper housing 12 and the lower housing 13 is completed, the top surface portion 12a and the bottom surface portion 13a are disposed to face each other, and the side surface portion 13b of the lower housing 13 is closely contacted and inserted into the side surface portion 12b of the upper housing 12.

The matching layer 300 provides a function of minimizing an air gap between the titanium package 11 and the power generating device module 100'. That is, since ultrasonic wave cannot penetrate an air gap, the matching layer 300 is provided to prevent ultrasonic wave from being reflected in the air gap and unable to reach the power generating device module. The matching layer 300 is disposed between the titanium package 11 and the power generating device module 100' and closely disposed to the titanium package 11 at the least, and accordingly, the transmission efficiency of ultrasonic wave that passes through the titanium package 11 may be increased.

Here, the matching layer 300 may have a conductive property and may be formed of a predetermined fluid excluding gas, and particularly, may be formed of any one of a fluid solid, a semi-solid, and a liquid. A material usable as any one of the fluid solid, the semi-solid and the liquid may be, for example, water, ultrasonic gel, silicone oil, and the like. Any one of the fluid solid, the semi-solid and the liquid may have a small change in viscosity, a large volume expansion rate, a small thermal conductivity, chemical resistance, and excellent electrical property.

When one or both of the acoustic impedance and the thickness of the matching layer 300 are adjusted, the transmission efficiency of ultrasonic wave may be maximized. The acoustic impedance of the matching layer 300 is represented by Equation 1 below.

$$Z_M = \sqrt{(Z_{Ti} Z_{TENG})} \quad \text{[Equation 1]}$$

$Z_M$: Acoustic impedance of the matching layer $Z_{Ti}$: Acoustic impedance of the titanium package≈27.3 Mrayls $Z_{TENG}$: Acoustic impedance of the power generating device module≈3 Mrayls $tM=\lambda/4$ (tM: thickness of the matching layer, $\lambda$: wavelength of ultrasonic wave)

The matching layer 300 may include a fine particle additionally to adjust the acoustic impedance. For example, the fine particle may include $TiO_2$ particles, Au particles, and the like.

The power generating device module 100' according to the present disclosure has either a single electrode 110 structure or a double electrode 120 structure selectively.

Referring to FIG. 3A, the power generating device module may have the single electrode 110 structure. The power generating device of the single electrode 110 may include the matching layer 300, a first friction member 113, a second friction member 115, a lower electrode 111, and a substrate 116. In this case, the matching layer 300 may be formed of a conductive material and have a function of an upper electrode.

The first friction member 113 is a type of a thin vibration film and generates a displacement in a longitudinal direction (or vertical direction) by ultrasonic wave. Here, the generation of the displacement means a production of electricity while a vibration occurs.

The first friction member 113 may apply a Perfluoroalkoxy alkane (PFA) film of a thickness of about 25 μm and have a roughly square shape in a plan view.

A material of the first friction member 113 may include Perfluoroalkoxy (PFA), Polytetrafluoroethylene (PTFE), Fluorinated ethylene propylene (FEP), Nylon, Styrene-Ethylene-Butylene-Styrene (SEBS), thin metal plate, and the like.

The lower electrode 111 may be integrally formed on the substrate 116 and may be formed of any material of metal or synthetic resin having conductivity such as gold (Au), silver (Ag), aluminum (Al), copper (Cu), and a conductive polymer.

As the substrate 116, a printed circuit board (PCB), a flexible PCB based on PI, a SEBS, and the like may be applied. Alternatively, the substrate 116 may be made of a polymer harmless to the human body, for example, Teflon may be used, but not limited thereto.

Accordingly, when ultrasonic wave is provided externally, the first friction member 113 and the second friction member 115 repeatedly contact and non-contact to generate electricity.

Referring to FIG. 3B, the power generating device module may have another single electrode 110 structure. The power generating device module of the single electrode 110 may include the first friction member 113, the second friction member 115, the lower electrode 111, the substrate 116, and a reference electrode 112. In this case, the matching layer 300 may not be formed of a conductive material.

The lower electrode 111 may be integrally formed on the substrate 116 and may be separately disposed from the reference electrode 112 disposed on a bottom of the substrate 116.

Moreover, the power generating device may have the double electrode 120 structure. The power generating device module of the double electrode 120 may include the matching layer 300, an upper electrode 301, the first friction member 113, the second friction member 115, the lower electrode 111, and the substrate 116. The structure of the double electrode 120 may be a structure of a pair of two electrodes. Hereinafter, the same reference numerals shown as the above-mentioned reference numerals may have the same configuration, and redundant descriptions will be omitted in the case of the same configuration.

The matching layer 300 may be provided on the first friction member 113, and the lower electrode 111 may be provided on the substrate 116 at the lower portion of the second friction member 115.

The double electrode 120 structure may be applied to the power generating device, and hereinafter, only the power generating device module having the single electrode 110 structure will be described. Of course, in the case that the lower electrode 111 is provided on the bottom of the second friction member 115 while the upper electrode 301 is provided on the first friction member 113, either one of the first friction member 113 or the second friction member 115 may be selectively omitted.

The first friction member 113 and the second friction member 115 are made of materials having different frictional charging properties, and it is preferable that a difference of the charging properties is greater on the charging property list.

More preferably, while the first friction member 113 is made of a metal, and the second friction member 115 is made of a polymer such that the frictional electrical properties may be excellent. In the present disclosure, the first friction member 113 vibrates using a high acoustic impedance mismatching property, and the triboelectricity is generated, and in this case, a pair of a polymer film and a metal is preferable to perform high acoustic impedance mismatching.

In other words, ultrasonic waves have different degrees of transmission depending on acoustic impedance properties of a medium, and a pressure change between the polymer film having a non-conductive property and the metal may be generated by artificially controlling such a difference in acoustic impedance. In the power generating device 100 of the present disclosure, such a pressure change is applied to convert a change in capacitance value due to a positional shift of the friction member 113 or 115 due to ultrasonic waves into electrical energy, thereby enabling energy generation in a body.

In addition, the power generating device 100 according to the present disclosure may include a sealing member 117 extended to cover from a front end of the storage block 12c to the substrate 116. The sealing member 117 may seal the power generating device module 100' on the storage block 12c and simultaneously, have a function of attaching the substrate 116 and the lower housing 13.

The power generating device 100 includes a silicon head 118 for connecting a bottom surface of the lower housing 13 and a lower front end of the side surface portion 12b of the upper housing 12 integrally. The silicon head 118 may be positioned on a line extending from the coating layer described above. In addition, although it is not shown in the drawing, the silicon head 118 may be selectively disposed on at least one surface (e.g., top surface, side surface, and bottom surface) of the outer surface of the titanium package 11, and not limited to the bottom surface position of the lower housing 13.

The cuff electrode may be connected through a feedthrough (FT) to transmit the electricity generated by the generating device module 100' to the cuff electrode 200 (refer to FIG. 1) of the silicon head 118 and outside of the lower housing 13. Of course, the position of the feedthrough (FT) connected to the cuff electrode may also be changed depending on the position of the silicon head 118.

Figure 5A:
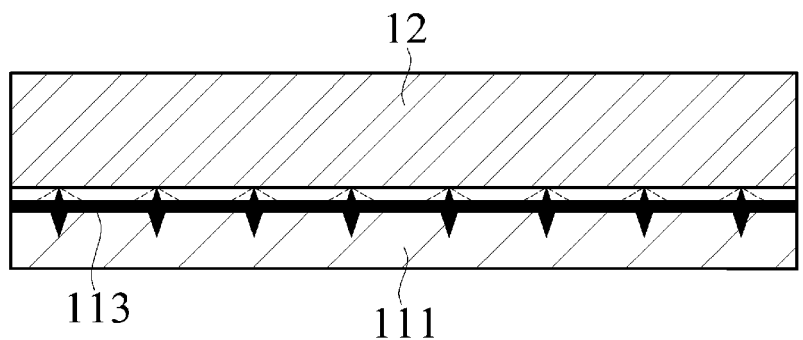
FIGS. 5A and 5B are reference diagrams illustrating an interface of the power generating device of the present disclosure.
Figure 5B:
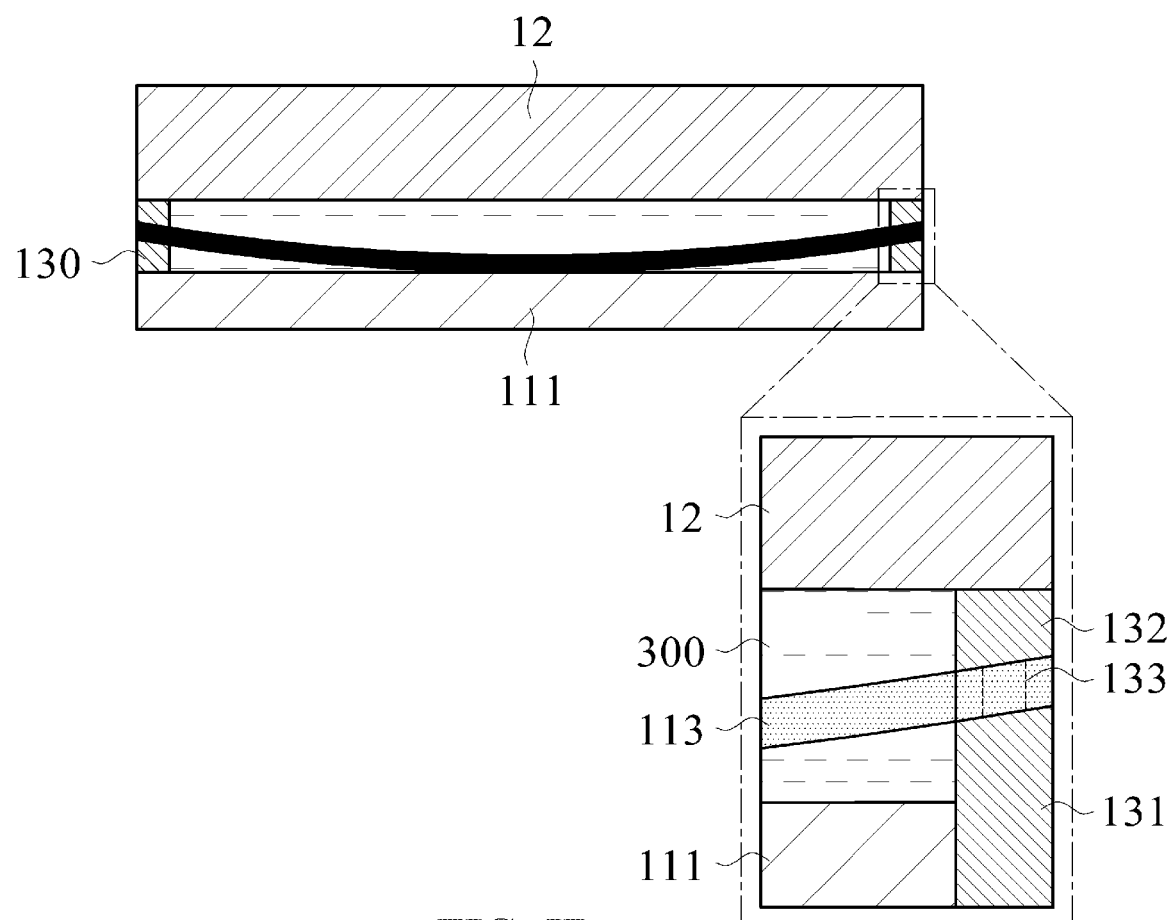
Figure 6:
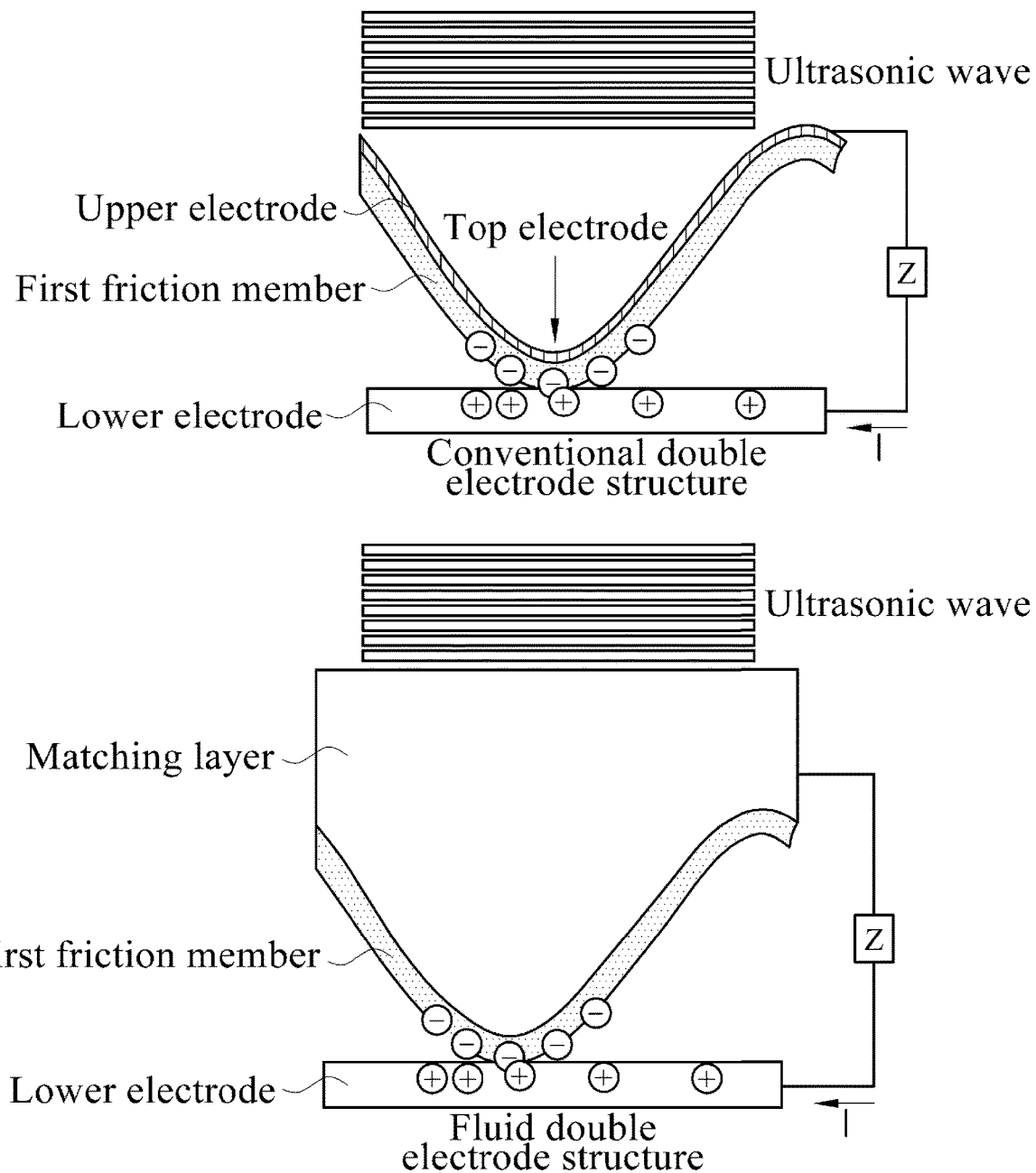
FIG. 6 is a reference diagram illustrating a periphery of the fluid matching layer of the present disclosure.

FIGS. 5A and 5B are reference diagrams illustrating an interface of the power generating device of the present disclosure, and FIG. 6 is a reference diagram illustrating a periphery of the fluid matching layer of the present disclosure.

Referring to FIGS. 5A and 5B and FIG. 6, the power generating device 100 of the present disclosure further includes a spacer 130.

The spacer 130 is provided between the upper housing 12 and the lower electrode 111 and includes a lower supporting member 131, an upper supporting member 132, and a connection member 133.

The lower supporting member 131 may support a portion between the first friction member 113 and the lower electrode 111. The lower supporting member 131 may provide a function of a general spacer.

The upper supporting member 132 may support a portion between the first friction member 113 and the upper housing 12. The upper support member 132 may provide a function of maintaining a height of the space to be accommodated in the accommodation space, which is a predetermined fluid excluding gas, and preventing a linear movement inside the accommodation space by pressure while the outer shape of the matching layer 300 is deformed.

Although not illustrated in the drawing, the spacer 130 may be provided in a structure protruding in a plurality of patterns toward the power generating device module 100' within the accommodation space of the upper housing 12 or in a plurality of patterns toward the inner bottom surface of the top surface 12a (refer to FIG. 2) of the upper housing 12 on the lower electrode 111, or a combination thereof.

The connection member 133 may be disposed through at least a portion of the first friction member 113 to connect the lower support member 131 and the upper support member 132.

Here, the spacer 130 may be constructed as one body, or each of the lower support member 131 and the upper support member 132 may be manufactured and assembled. Of course, the connection member 133 may be integrally provided on any one of the upper support member 132 and the lower support member 131 and may be coupled (or attached or fixed) to the other one through the first friction member 113 during the assembly process.

As shown in FIG. 6, in the case that the existing double electrode structure is changed to the fluid double electrode structure to which the matching layer 300 is applied, there is an effect that it is possible to solve the problem of deteriorating adhesion while the upper electrode vibrates together with the first friction member, and it is possible to solve the problem of oxidizing the upper electrode or causing cracks due to vibration. Of course, in the fluid double electrode structure, since the matching layer is made of a conductive material and a predetermined fluid excluding gas, there is no need to consider the adhesion of the upper housing and the first friction material, so the problem of poor adhesion or cracks of the existing upper electrode may be fundamentally prevented, and the effect of three birds with one stone may be expected because the transmission efficiency of ultrasonic wave may be maximized.

Figures 7A, 7B:
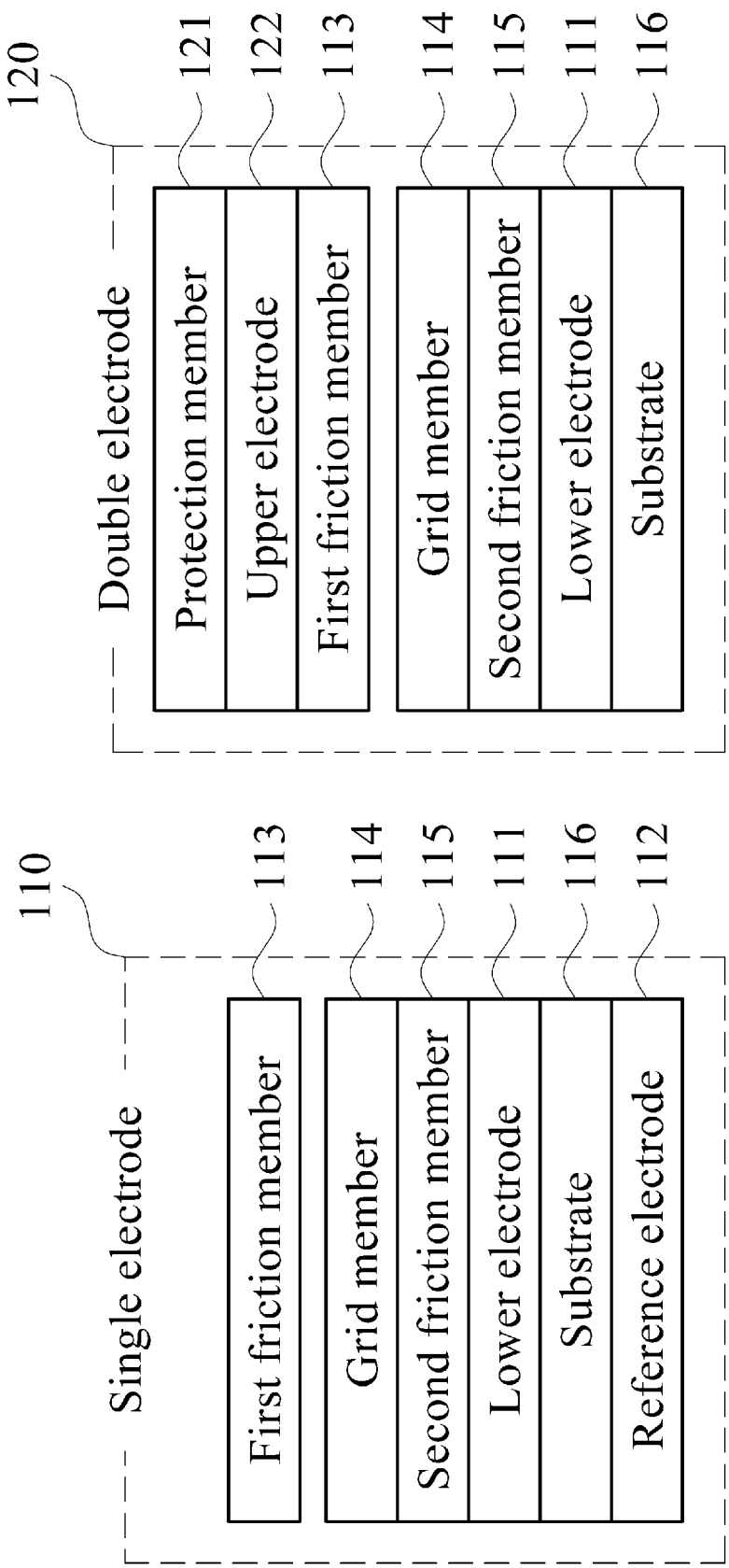
FIGS. 7A and 7B are block diagrams illustrating an ultrasonic triboelectric generating device using a resonance-based grid structure according to the present disclosure.
Figure 8A:
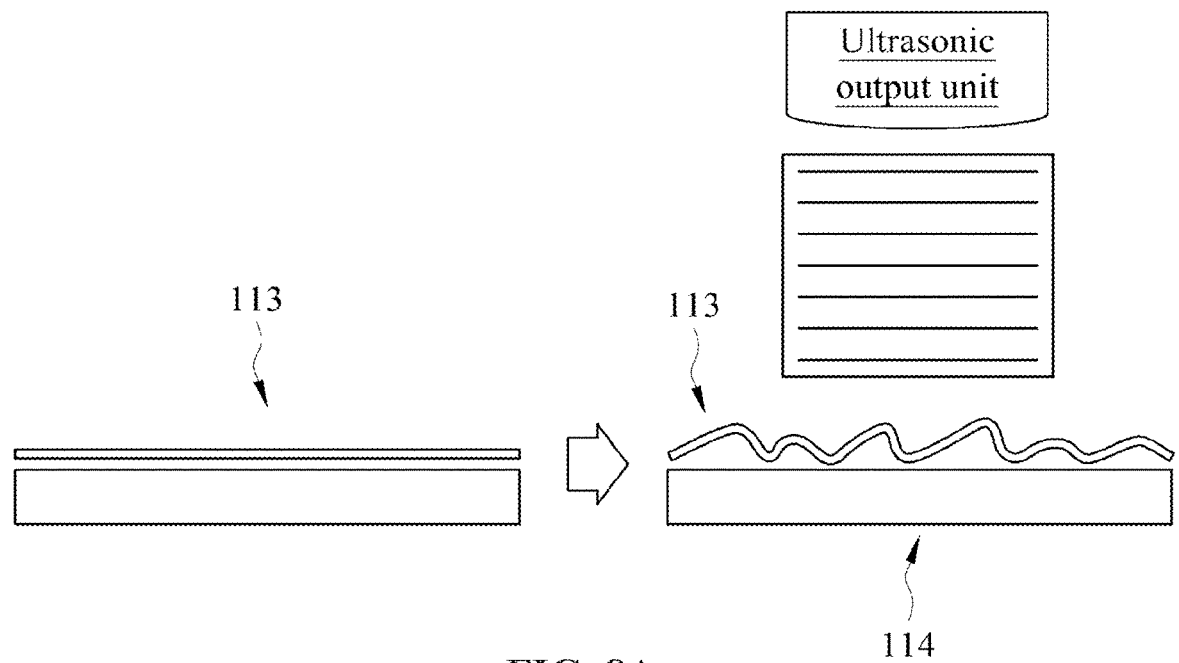
FIGS. 8A and 8B are reference diagrams illustrating a resonating state of an ultrasonic triboelectric generating device using a resonance-based grid structure according to the present disclosure.
Figure 8B:
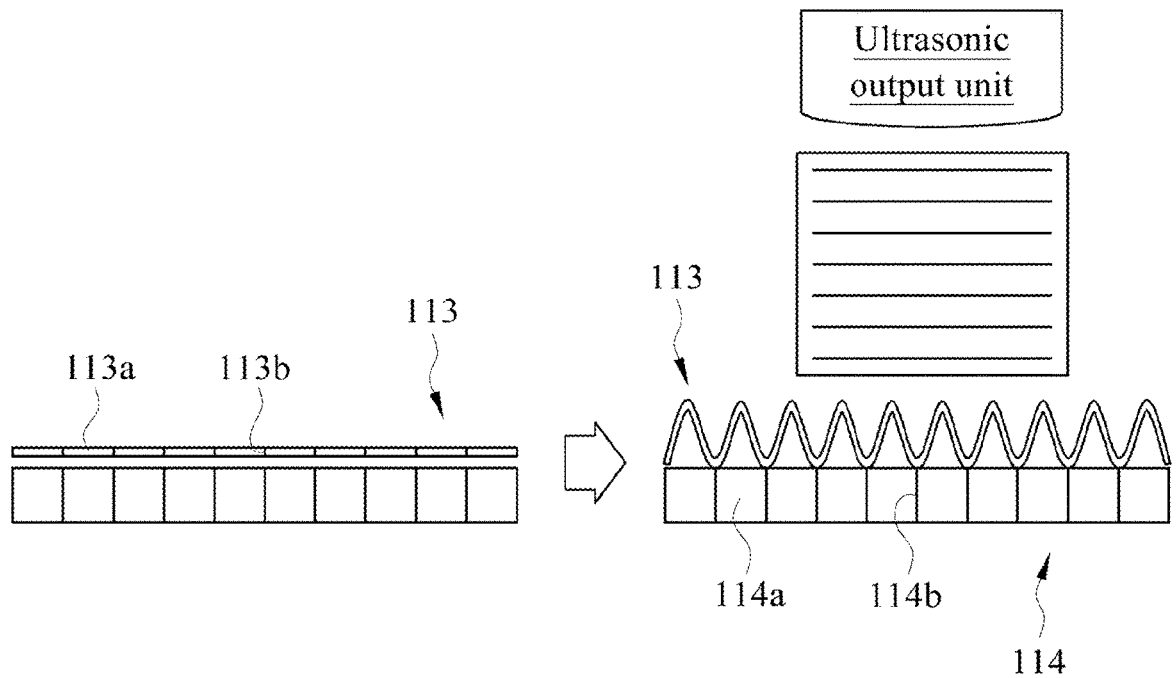
Figure 9:
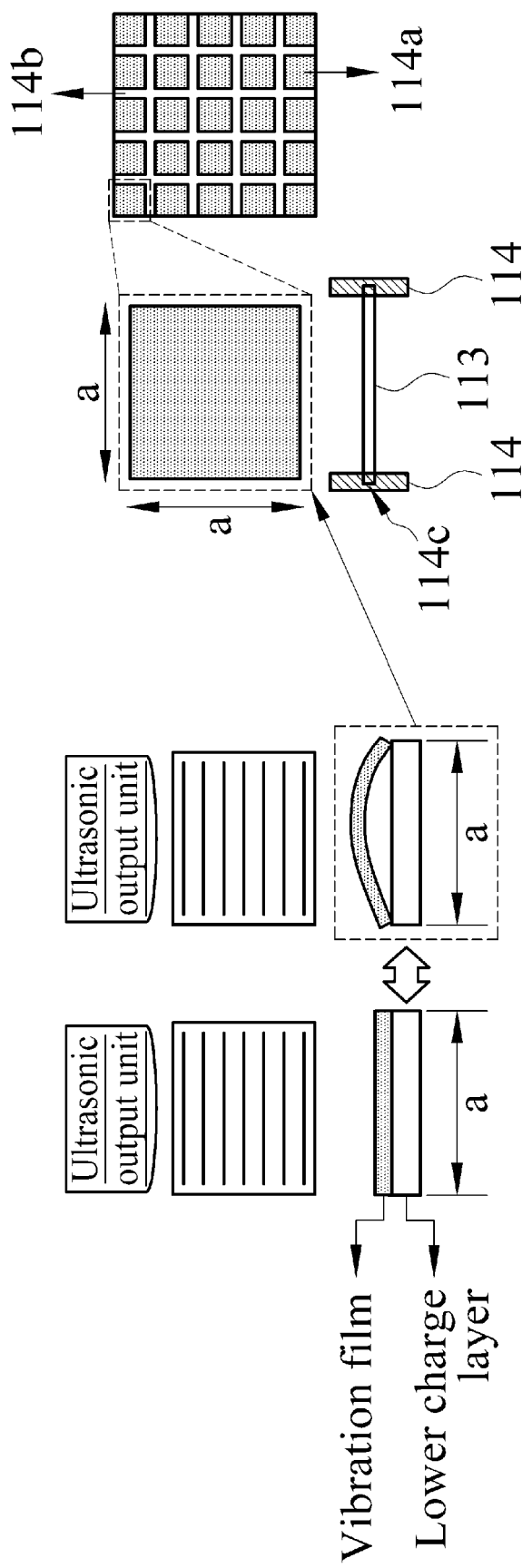
FIG. 9 is a reference diagram illustrating a state that ultrasonic wave is provided to an ultrasonic triboelectric generating device using a resonance-based grid structure according to the present disclosure.

FIGS. 7A and 7B are block diagrams illustrating an ultrasonic triboelectric generating device using a resonance-based grid structure according to the present disclosure. FIGS. 8A and 8B are reference diagrams illustrating a resonating state of an ultrasonic triboelectric generating device using a resonance-based grid structure according to the present disclosure. FIG. 9 is a reference diagram illustrating a state that ultrasonic wave is provided to an ultrasonic triboelectric generating device using a resonance-based grid structure according to the present disclosure.

The power generating device 100 according to the present disclosure includes either one of the single electrode 110 structure or the double electrode 120 structure selectively.

Referring to FIG. 7A, the power generating device 100 may have the single electrode 110 structure. The power generating device 100 of the single electrode 110 may include a single lower electrode 111 and a single reference electrode 112.

The power generating device of the single electrode structure may include the first friction member 113, the grid member 114, the second friction member 115, the lower electrode 111, the substrate 116, and the reference electrode 112.

The first friction member 113 is a type of a thin vibration film and generates a displacement in a longitudinal direction (or vertical direction) by ultrasonic wave as shown in FIG. 8B. Here, the generation of the displacement means a production of electricity while a vibration occurs. In the case that the first friction member 113 is disposed at an outermost position, the first friction member 113 may have a function of a protective layer.

The first friction member 113 may apply a Perfluoroalkoxy alkane (PFA) film of a thickness of about 25 μm and have a square shape in a plan view.

The first friction member 113 may adjust a form factor in consideration of the influence of a transmission medium such as water or gel, an ultrasonic pressure, and an electrostatic attraction between the film and the lower electrode. In addition, when connected to the resonance structure using the grid member 114, a first displacement area 113a on the first friction member 113 corresponding to a vibration area 114a on the grid member 114 may be expanded.

A material of the first friction member 113 may include Perfluoroalkoxy (PFA), Polytetrafluoroethylene (PTFE), Fluorinated ethylene propylene (FEP), Nylon, Styrene-Ethylene-Butylene-Styrene (SEBS), thin metal plate, and the like.

The grid member 114 may provide a function of simply supporting the first friction member 113 or fixedly supporting the first friction member 113 by attachment on the lower electrode 111. The grid member 114 forms a grid pattern, for example, but not limited thereto, and may have either one pattern of an equilateral polygon with at least a triangle or circle. The grid member 114 may be made of Polydimethylsiloxane (PDMS), Polymethylmethacrylate (PMMA), polyisoprene, or the like, and it is preferable to be made of attachable or supportable material.

The grid member 114 may have a function of a protrusion 114' (refer to FIG. 10) such that the first friction member 113 is spaced apart from the lower electrode 111. Of course, only when the protrusion 114' is required, the grid member may be selectively applied as a structure including the function of the protrusion 114', or may be additionally provided on the fixed area 114b on the grid member 114 to be described below through a structure in which a separate component from the grid member 114 is attached, coupled, and assembled.

In the case that a thickness of the first friction member 113 is 25 μm, each vibration area 114a of the grid member 114 may be formed of a grid pattern having a horizontal and vertical length of about 1 mm, respectively.

A length of one side of the grid member 114 may vary depending on physical properties such as thickness, Young's modulus, and the like.

For example, a length of one side of the vibration area 114a of the grid member 114 may be calculated with reference to the thickness 25 μm as below.

[Equation 2]
$$f_{11} = \frac{\lambda_{11}^2}{2\pi a^2} \sqrt{\frac{Eh^3}{12\gamma(1-v^2)}} =$$
$$\frac{35.99}{2\pi a^2} \times \sqrt{\frac{(0.517 \text{GPa}) \times (25\mu\text{m})^3}{12 \times (215 \times 25\mu\text{m}) \times (1-0.45^2)}}$$
$$\therefore \text{Fixed edge } a = \sqrt{\frac{0.0219}{f_{11}}}$$

λ: dimensionless frequency parameter (function of the B.C at the edge of the plate)
a: length
E: elastic modulus
h: thickness
γ: mass per unit area (density×h)
v: Poisson ratio Accordingly, the length of one side of the vibration area 114a is derived to be about 1 mm in 20 kHz.

The second friction member 115 may be provided in an optional element that may be omitted, and may implement the same function as the first friction member 113 described above. The second friction member 115 may also be provided with the function of the protrusion 114' through the grid member 114.

The lower electrode 111 may be integrally implemented on the substrate 116, and may be spaced apart from the reference electrode 112 disposed under the substrate 116. The lower electrode 111 may be implemented of any material including a conductive metal such as gold (Au), silver (Ag), aluminum (Al), copper (Cu), a conductive polymer, and the like to induce electric charges.

The substrate 116 may be a printed circuit board (PCB) or PI-based flexible PCB, SEBS, or the like. Alternatively, the substrate may be made of a polymer harmless to the human body, for example, Teflon may be used, but is not limited thereto.

Referring to FIG. 7B, the power generating device may have the double electrode 120 structure. The power generating device of the double electrode 120 may have a structure in which two electrodes form a pair. Hereinafter, reference numerals identical to those denoted above may have the same configuration, and redundant descriptions are omitted in case of the same configuration.

The double electrode 120 structure of the power generating device includes a protection member 121, an upper electrode 122, the first friction member 113, the grid member 114, the second friction member 115, the lower electrode 111, and the substrate 116.

In this case, since the first friction member 113 is additionally provided with the protection member 121 at the outside, the function of the protection layer is lost. Also, in the case that the first friction member 113 is made of a non-conductive material, the upper electrode 122 is provided on the first friction member 113, the lower electrode 111 is provided on the substrate 116 at the bottom of the second friction member 115, and the reference electrode 112 is provided under the substrate 116. Of course, in the case that the first friction member 133 is conductive and thus may function as an electrode, the upper electrode 122 and the reference electrode 112 may be omitted.

The power generating element may be applied to the structure of the double electrode 120, and only the power generating element having the structure of the single electrode 110 will be described below.

Furthermore, the upper electrode may be made of any material including a conductive metal such as gold (Au), silver (Ag), aluminum (Al), copper (Cu), or a conductive polymer to induce electric charges like the lower electrode.

As shown in FIG. 8A, in the case that the first friction member 113 is constructed as one element, there is a limit to generating a regular displacement in the first friction member 113 when ultrasonic waves are provided.

On the other hand, as shown in FIG. 8B, in the case that the first friction member 113 is divided into a plurality of first displacement areas 113a to correspond to the vibration area 114a of the grid member 114, the ultrasonic triboelectric generating device 100 using a resonance-based grid structure generates constant and strong displacement using the resonance by ultrasonic waves provided from the ultrasonic output unit.

The element of reference numeral '114c' not described in FIG. 9 shows a stepped portion 114c formed in the internal vibration area 114a of the grid member 114. The stepped portion 114c is a portion in which the first friction member 113 is inserted and seated in the vibration area 114a, and the horizontal width of the fixed area 114b may be different from each other with respect to the vertical direction. Alternatively, the stepped portion 114c may have a groove structure that is concavely recessed along the edge of the first friction member 113 on the fixed area 114b. Of course, in the case that the first friction member 113 is placed on the front end of the grid member 114, a stepped portion (not shown) may be formed on the front end of the grid member 114.

Alternatively, although not shown in the drawing, since the grid member 114 is formed in two layers in the same shape, the first friction member 113 may be placed on the upper end of the lower grid member (not shown), and the upper grid member (not shown) may be placed on the upper part of the lower grid member to prevent the first friction member 113 from being separated. In this case, the heights of the upper grid member and the lower grid member may be selectively formed according to the installation height of the first friction member 113.

Figure 10:
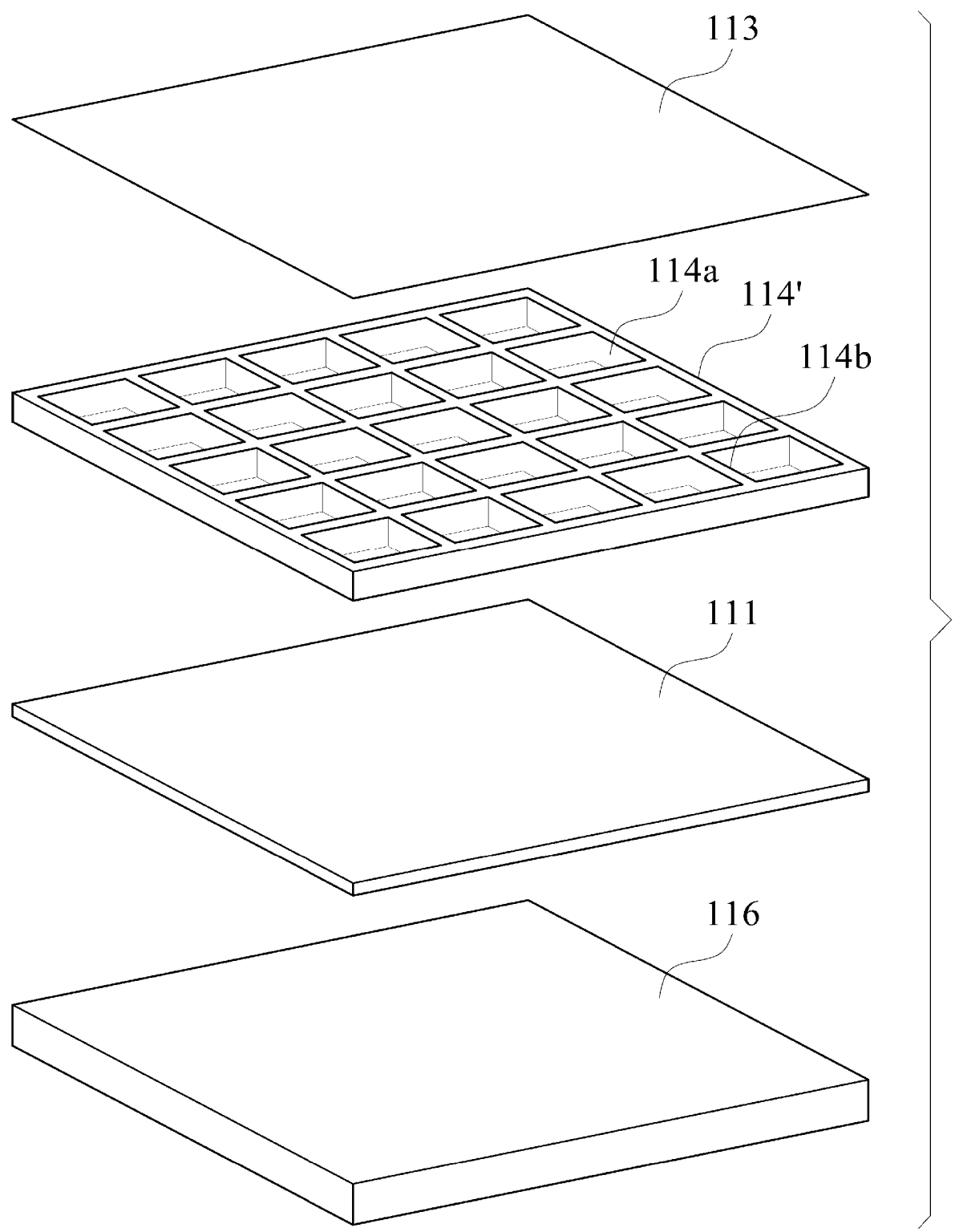
FIGS. 10 and 11 are exploded perspective diagrams illustrating an ultrasonic triboelectric generating device using a resonance-based grid structure.
Figure 11:
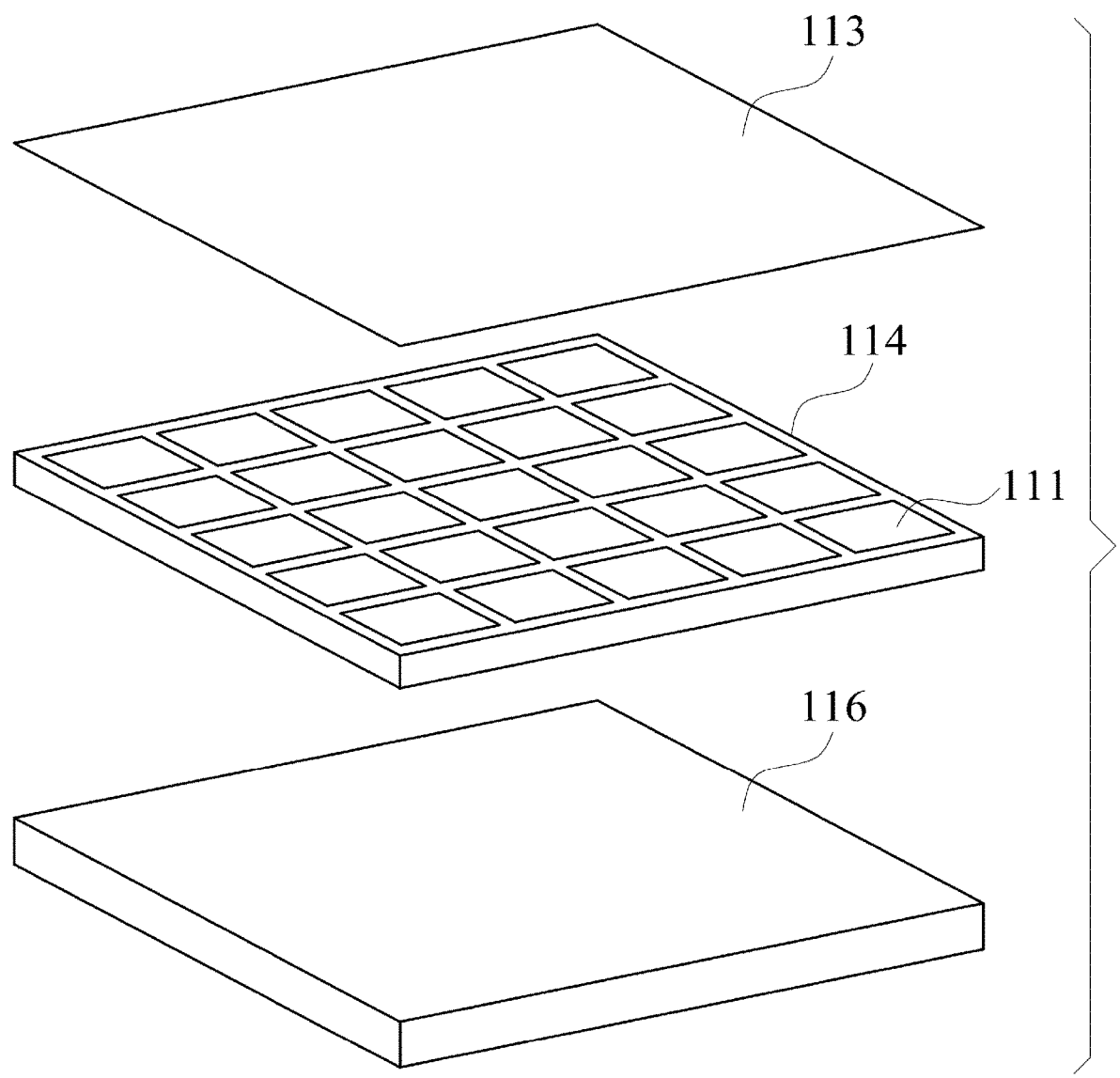

FIGS. 10 and 11 are exploded perspective diagrams illustrating an ultrasonic triboelectric generating device using a resonance-based grid structure.

FIG. 10 shows a power generating device of a single electrode having a protrusion, and FIG. 11 shows a power generating device of a single electrode without a protrusion.

The difference according to the presence of the protrusion 114' lies in whether the grid member 114 provides a gap between the first friction member 113 and the lower electrode in the vibration area 114a.

Since the protrusion 114' providing a gap between the first friction member 113 and the lower electrode 111 has a structure that is selectively applied, the detailed description thereof is redundant and omitted.

Figure 12A:
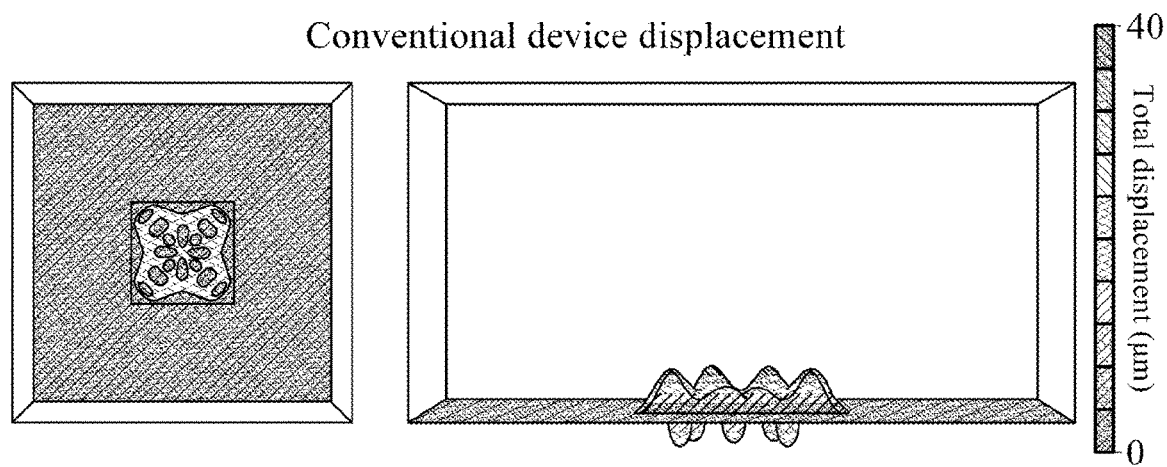
FIGS. 12A and 12B are three-dimensional graphs illustrating a displacement of an ultrasonic triboelectric generating device using a resonance-based grid structure according to the present disclosure.
Figure 12B:
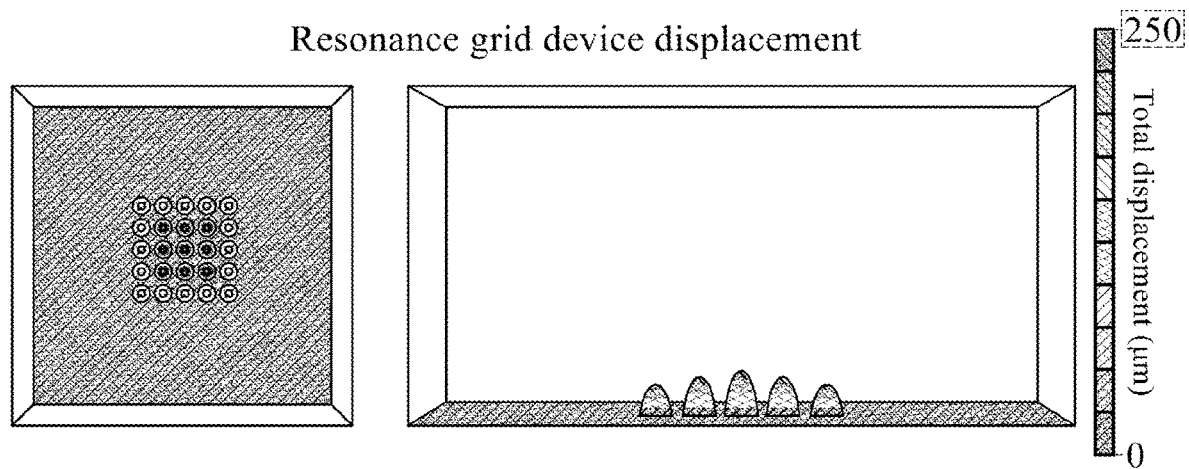

FIGS. 12A and 12B are three-dimensional graphs illustrating a displacement of an ultrasonic triboelectric generating device using a resonance-based grid structure according to the present disclosure.

Referring to FIGS. 12A and 12B, FIG. 12A shows a displacement of the conventional power generating device, and FIG. 12B shows a displacement of the ultrasonic triboelectric generating device using a resonance-based grid structure.

The conventional power generation device of FIG. 12A generates a displacement while following a roughly square or circular band when viewed on a plane, and the maximum displacement is approximately 40 µm. In addition, the displacement viewed from the front represents a structure representing upward and downward on a reference plane, in which energy due to the displacement is partially offset, and the relatively greater displacement expressed at the top is determined to have difficulty in setting the reference point for displacement caused by a clear displacement difference between the center and the outside.

On the other hand, the resonant power generating device of FIG. 12B may accurately determine a position of the displacement by generating a displacement in which a circular pattern of about row and column is accurately expressed when viewed on a plane, and the maximum displacement is approximately 250 µm, resulting in a strong displacement of about six times more than that of the conventional device. In addition, the displacement viewed from the front shows a structure in which energy is transferred only by the upper part of the reference plane, and it is determined that setting a reference point for displacement is easy because the displacements protruding from the upper portion have a direction in which the displacement difference increases toward the center.

Here, since the maximum voltage (open-circuit voltage) of the power generating device is proportional to the displacement, an increase in the power generating voltage due to the increase in the displacement may be expected. This proportional relationship may be derived through Equation 3 below.

$$V_{oc} = \frac{\sigma \chi(t)}{\varepsilon_a} \qquad \text{[Equation 3]}$$

$V_{oc}$: triboelectric generating device voltage (Open circuit Voltage)
σ: surface change (vibration film surface charge)
$\chi(t)$: displacement depending on a time (displacement of the vibration film)
$\varepsilon_0$: Vacuum permittivity FIG. 13 is a three-dimensional graph illustrating a displacement for each frequency of the present disclosure.

Figure 13:
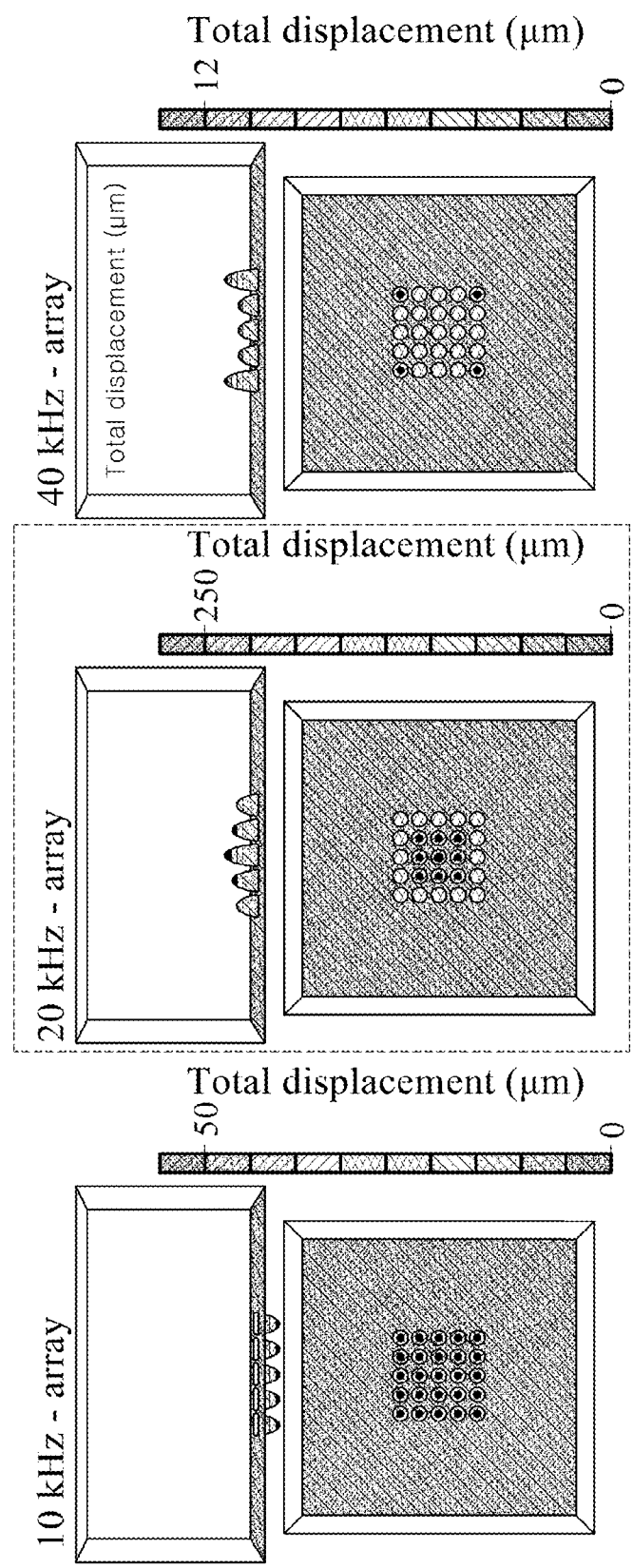
FIG. 13 is a three-dimensional graph illustrating a displacement for each frequency of the present disclosure.

Referring to FIG. 13, FIG. 13 (a) shows a displacement using a frequency of 10 kHz, FIG. 13 (b) shows a displacement using a frequency of 20 kHz, and FIG. 13 (c) shows a displacement using a frequency of 40 kHz.

FIG. 13 (a) shows that the displacement is generated only in the lower direction of the reference plane. In addition, the heights of each displacement are almost constant, and the size of each displacement is formed to be about 50 µm.

FIG. 13 (b) shows that the displacement occurs only in the upper direction of the reference plane, and the size of each displacement increases toward the center, and the size of the maximum displacement is about 250 µm.

FIG. 13 (c) shows the displacement occurs only in the upper direction of the reference plane, and the size of each displacement is largest in the outer corner region, and the size decreases toward the center. The maximum displacement in the outer corner region is formed to be about 12 µm.

Comparing these, it is identified that the greatest displacement occurs in the frequency range of 20 kHz in FIG. 13 (b), and a relatively uniform displacement is provided.

Figure 14:
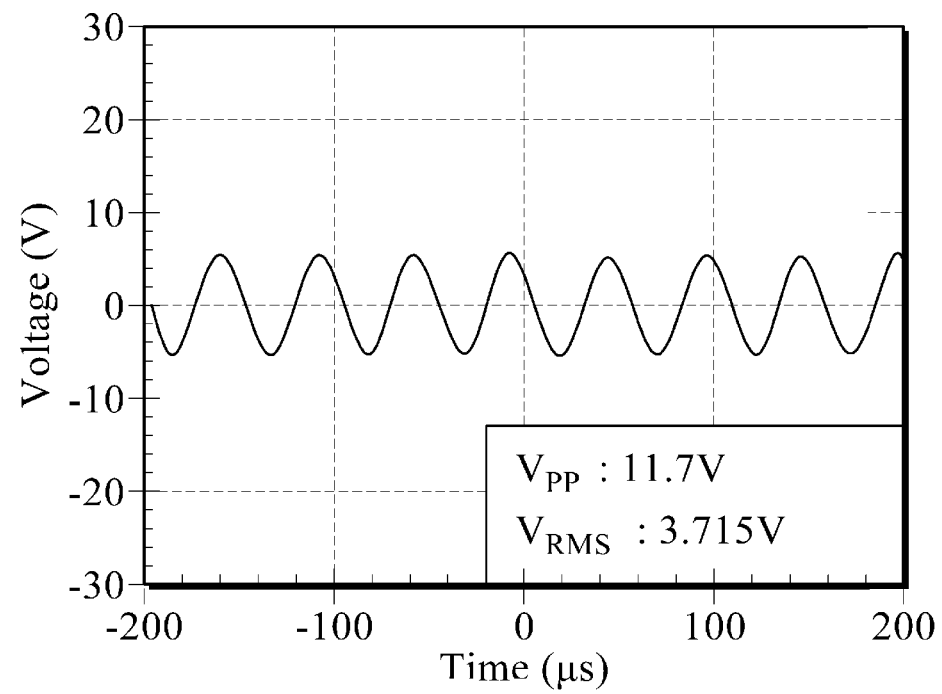
FIG. 14 is a graph illustrating an output of an ultrasonic triboelectric generating device using a resonance-based grid structure according to the present disclosure.
Figure 14:
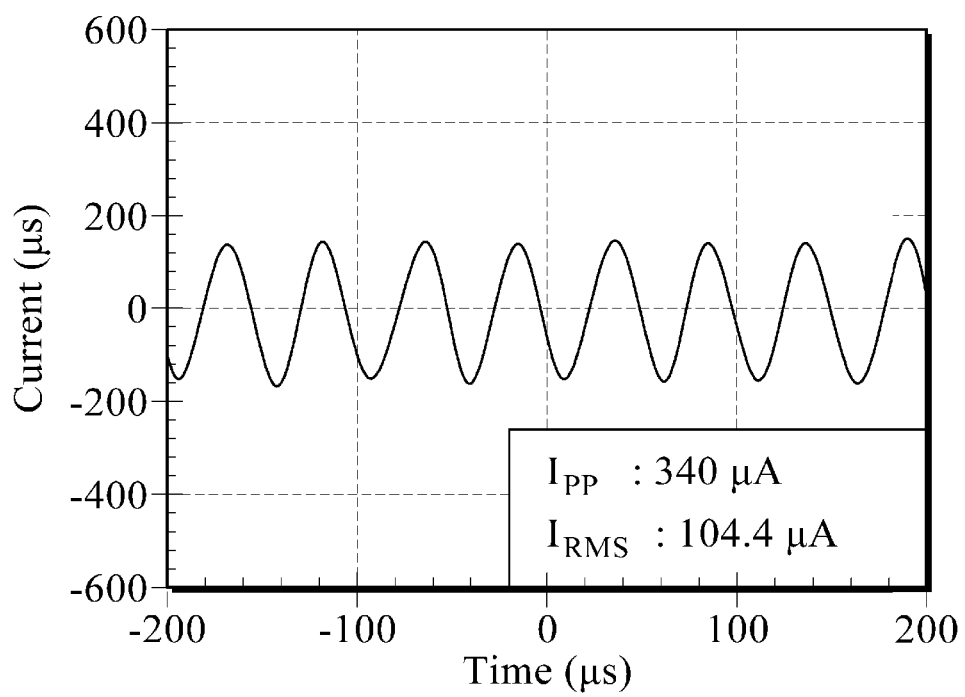

FIG. 14 is a graph illustrating an output of an ultrasonic triboelectric generating device using a resonance-based grid structure according to the present disclosure.

FIG. 14 shows voltage and current values generated when the frequency of ultrasonic waves is set to 20 kHz as described above.

The maximum voltage is 11.7 V, and a voltage of 10 V (peak to peak) or more may be generated, and the current may generate 340 μA (peak to peak).

This output is the result of utilizing a micro power generating device of 5 (width)×5 (length) 25 mm$^2$, indicating that the micro power generating device may generate a voltage necessary for pain relief in a deep part of the body.

Figure 15:
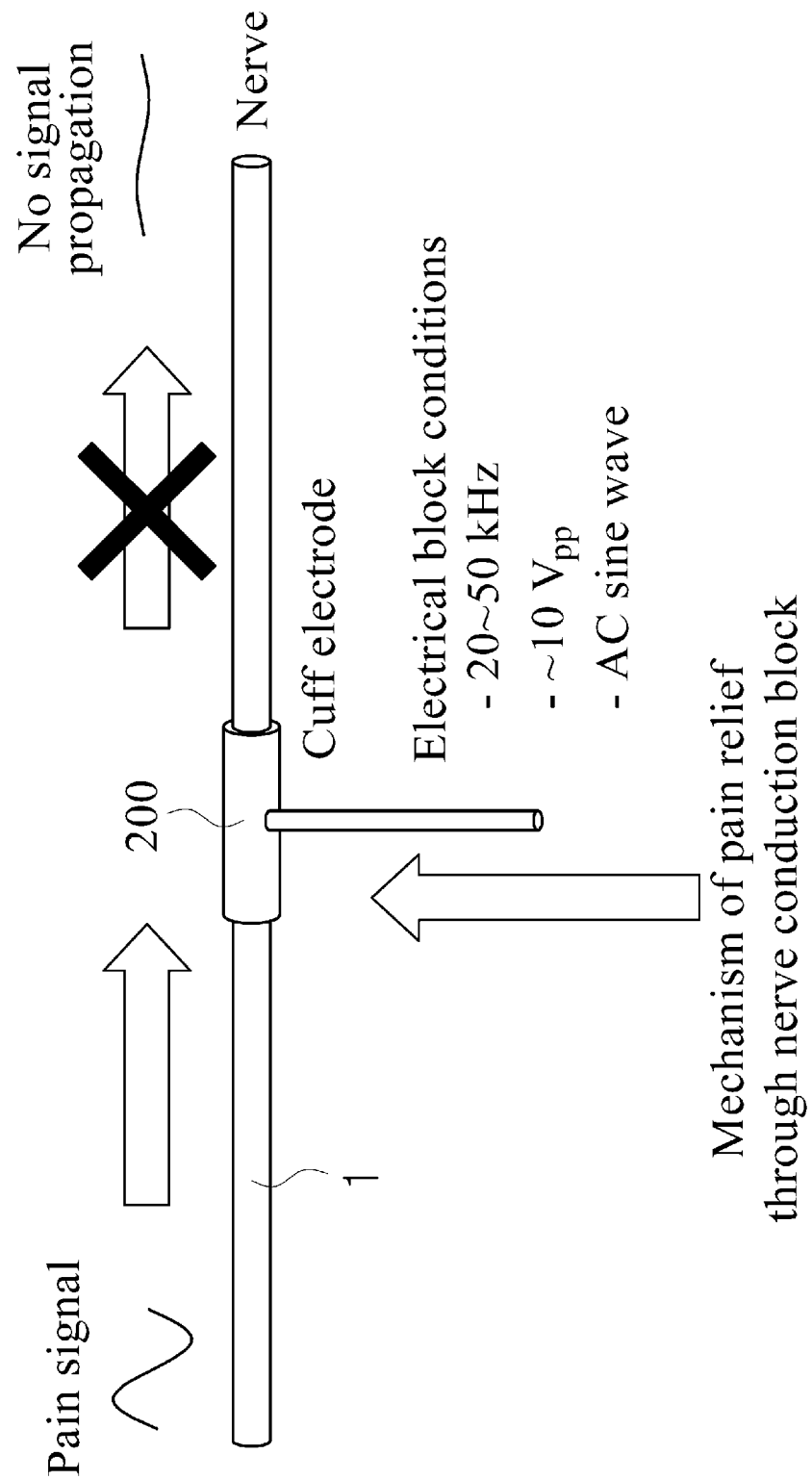
FIG. 15 is a schematic application diagram of an electroceutical for nerve stimulation according to the present disclosure.

FIG. 15 is a reference diagram illustrating a schematic mechanism of an electroceutical provided with an ultrasonic triboelectric generating device according to the present disclosure.

Referring to FIG. 15, a process of transmitting a pain signal from the left to the right brain through a nerve fiber 1 arranged to cross the center in the horizontal direction is shown.

As an exemplary embodiment, the cuff electrode 200 is mounted in the middle of the nerve fiber 1 through which the pain signal passes, for example, provides electrical stimulation generated from the power generating device 100 before the pain signal is transmitted to the brain, blocking or at least partially offsetting the pain signal to the brain, causing pain or minimal pain.

Of course, the power generating device 100 generating electrical stimulation may control pain by continuously providing electric stimulation of AC waveform to the nerve fiber 1 by receiving ultrasonic waves with a frequency in the range of about 20 to 50 kHz from the outside.

Also, in another embodiment, the nerve stimulation signal may apply electrical stimulation related to nerve activation, nerve blocking, recovery of nerves and/or cells, and regeneration to specific tissues or cells of the body. That is, parts, tissues, and cells of the body to which the nerve stimulation signal according to the present disclosure is applied are not specified to the brain.

Figure 16A:
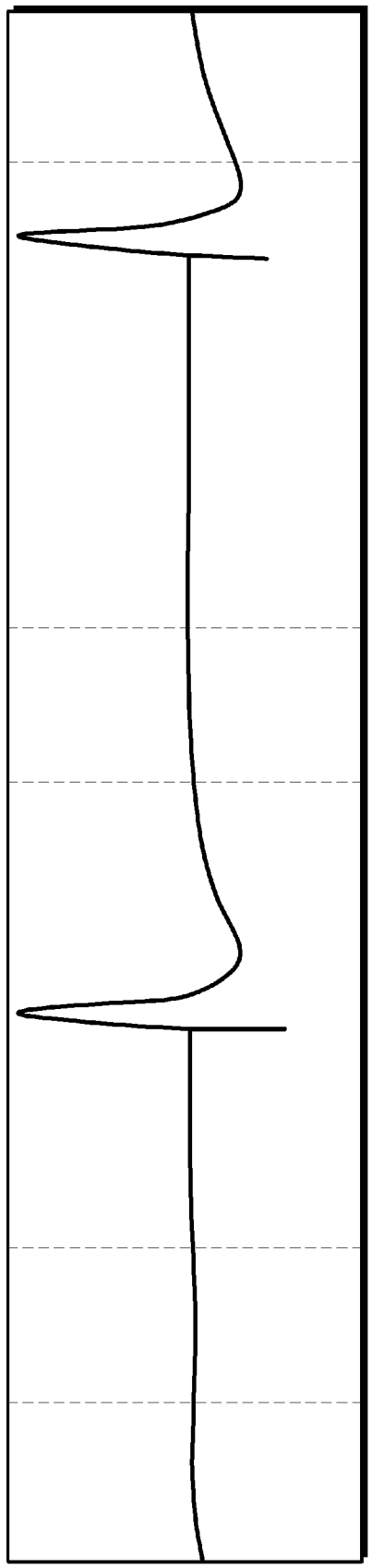
FIGS. 16A and 16B are graphs supporting an effect of an electroceutical for nerve stimulation of the present disclosure.
Figure 16B:
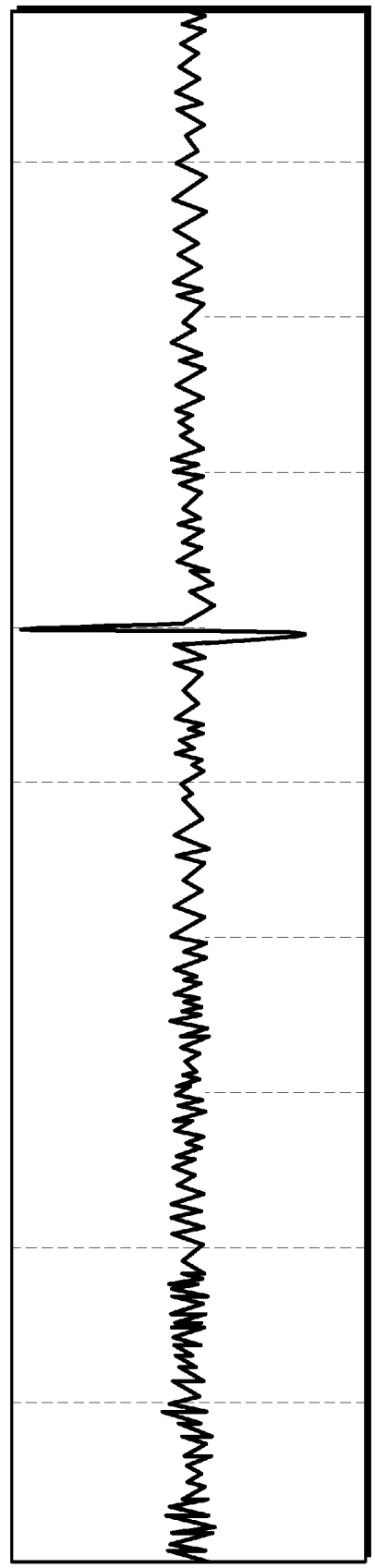

FIGS. 16A and 16B are graphs supporting an effect of an electroceutical for nerve stimulation of the present disclosure.

Referring to FIGS. 16A and 16B, FIG. 16A shows a signal when pain is transmitted to the brain before electrical stimulation is provided, and FIG. 16B shows a signal when pain is not transmitted to the brain by providing electrical stimulation.

FIG. 16A shows that the brain is intermittently feeling pain as the same pattern of pain signals appears periodically. FIG. 16B shows that the conduction block effect is provided by the electroceutical for nerve stimulation as the small waveform continues to be involved and the large waveform does not change even before and after the pain signal.

According to the problem to be solved of the present disclosure described above, the ultrasonic wave to be provided to the power generating device may be designed to correspond to the resonance frequency to maximize the power generation voltage, maximize the displacement of the power generating device in various frequency bands, uniformly adjust the amount of power generation for each vibration area of the friction member through the grid member, and improve the amount of power generation. The connection between the power generating device and the cuff electrode may at least partially block the direct transmission of pain signals to the brain on the nerve fiber, and the power may be transmitted stably from the deep inside of the body. While the power may be supplied to the deep inside of the body, a circuitry is unnecessary, and the small and lightweight of the device becomes available. Accordingly, it may be expected that the implantable electroceutical may solve periodic surgical problems or power depletion problems associated with battery replacement.

As described above, the ultrasonic triboelectric generating device and the electroceutical for nerve stimulation provided with the same may maximize the efficiency of ultrasonic waves to the power generating device while wrapping the outside of the power generating device module in a titanium package. The interfacial design that minimizes the air gap by applying the matching layer between the titanium package and the power generating device module may significantly increase the ultrasonic transmission efficiency by adjusting the acoustic impedance and thickness. By connecting the power generating device and the cuff electrode, the nerve may be stimulated from the deep inside of the body to the pinpoint. The power supply to the deep inside of the body becomes available without a circuitry, and the small and lightweight of the device becomes available, and accordingly, there is an effect that the implantable electroceutical may solve periodic surgical problems or power depletion problems associated with battery replacement.

Furthermore, the ultrasonic triboelectric generating device and the electroceutical for nerve stimulation provided with the same according to the present disclosure may maximize the power generation voltage by designing the ultrasonic waves to be provided to the power generating device to correspond to the resonance frequency, maximize the displacement of the power generating device in various frequency bands, and uniformly adjust the power generation amount for each vibration area of the friction member through the grid member.

Specific embodiments have been illustrated and described above to illustrate the technical inventive concept of the present disclosure, but the present disclosure is not limited to the construction and the effect of the specific embodiments as described above, and various modifications may be implemented within the scope of the present disclosure as long as not departing from the scope of the present disclosure. Therefore, such modifications need to be regarded as belonging to the scope of the present disclosure, and the scope of the present disclosure should be determined by appended claims to be described later.

What is claimed is:

1. An ultrasonic triboelectric generating device, comprising:
   a power generating device module comprising:
   a lower electrode; and
   a first friction member disposed on the lower electrode;
   a matching layer disposed on the first friction member; and
   a titanium package disposed to surround an outer periphery of the power generating device module, wherein the titanium package is attached to an upper portion of the matching layer and surrounding the matching layer,
   wherein the matching layer includes a fluid, is configured to function as an upper electrode, and
   wherein when an external ultrasonic wave is applied to the matching layer, displacement of the matching layer occurs only on a surface facing the lower electrode to have the power generating device module generate triboelectric electricity, wherein the titanium package includes:
- an upper housing disposed to surround an upper portion and a side portion of the power generating device module and attached to a side of the matching layer; and
- a lower housing partially inserted to the upper housing to surround a lower portion and the side portion of the power generating device module; and
- a spacer provided between the upper housing and the lower electrode, wherein the spacer includes:
- a lower supporting member positioned between the first friction member and the lower electrode;
- an upper supporting member positioned between the first friction member and the upper housing; and
- a connection member disposed at least partially penetrating the first friction member to connect between the lower supporting member and the upper supporting member.

2. The device of claim 1, wherein the upper housing includes a storage block downwardly protruded to surround the matching layer in an inner surface thereof facing the matching layer.

3. The device of claim 2, further comprising:
- a sealing member extended to cover the storage block; and
- a silicon head disposed on at least a side of an outer surface of the titanium package.

4. The device of claim 3, wherein the triboelectric electricity generated by the power generating device module is transmitted to the silicon head and outside of the lower housing.

5. The device of claim 1, wherein the first friction member generates the triboelectric electricity by friction with the lower electrode when the displacement is caused by the external ultrasonic wave.

6. The device of claim 1, wherein the matching layer is closely disposed to the first friction member, and a shape of the matching layer is deformed corresponding to a vibration of the first friction member.

7. An electroceutical, comprising:
- the ultrasonic triboelectric generating device according to claim 1; and
- a cuff electrode provided on a side of the titanium package and adapted to be mounted on a nerve fiber,
- wherein the ultrasonic triboelectric generating device is configured to, when a nerve stimulation signal is generated in the nerve fiber, generate the triboelectric electricity from the applied ultrasonic wave, and transfer the triboelectric electricity to the nerve fiber through the cuff electrode, to block a transmission of the nerve stimulation signal to a brain.

* * * * *